(12) United States Patent
Srinivas et al.

(10) Patent No.: US 11,286,352 B2
(45) Date of Patent: Mar. 29, 2022

(54) PROCESS FOR PREPARATION OF BEADS FOR IMAGING

(71) Applicant: STICHTING RADBOUD UNIVERSITAIR MEDISCH CENTRUM, Nijmegen (NL)

(72) Inventors: Mangala Srinivas, Nijmegen (NL); Olga Koshkina, Nijmegen (NL); Carl Gustav Figdor, Nijmegen (NL); Ingrid Jolanda Monique De Vries, Nijmegen (NL)

(73) Assignee: STICHTING RADBOUD UNIVERSITAIR MEDISCH CENTRUM, Nijmegen (NL)

( * ) Notice: Subject to any disclaimer, the term of this patent is extended or adjusted under 35 U.S.C. 154(b) by 711 days.

(21) Appl. No.: 16/083,576

(22) PCT Filed: Mar. 13, 2017

(86) PCT No.: PCT/EP2017/055827
§ 371 (c)(1),
(2) Date: Sep. 10, 2018

(87) PCT Pub. No.: WO2017/153605
PCT Pub. Date: Sep. 14, 2017

(65) Prior Publication Data
US 2019/0077925 A1    Mar. 14, 2019

(30) Foreign Application Priority Data
Mar. 11, 2016  (EP) .................... 16159884

(51) Int. Cl.
A61K 9/00         (2006.01)
C08J 3/205        (2006.01)
(Continued)

(52) U.S. Cl.
CPC .......... C08J 3/205 (2013.01); A61K 49/0002 (2013.01); A61K 49/1818 (2013.01);
(Continued)

(58) Field of Classification Search
CPC ....................................... C08J 3/205
See application file for complete search history.

(56) References Cited

U.S. PATENT DOCUMENTS

2010/0158815 A1   6/2010  Wang et al.
2011/0020139 A1   1/2011  Bulte et al.

FOREIGN PATENT DOCUMENTS

CN         101574530 A      11/2009
WO      2009028825 A2       3/2009
(Continued)

OTHER PUBLICATIONS

Srinivas M. et al., "Customizable, multi-functional fluorocarbon nanoparticles for quantitative in vivo imaging using 19F MRI and optical imaging", Biomaterials, 2010, pp. 7070-7077, vol. 31, No. 27, Elsevier Science Publishers, Barking,G.B.
(Continued)

Primary Examiner — Paul W Dickinson
(74) Attorney, Agent, or Firm — Hudak, Shunk & Farine Co. LPA

(57) ABSTRACT

A process for the preparation of beads including a biocompatible hydrophobic polymer, a perfluorocarbon, polyvinylalcohol and optionally a metal compound, including the steps of: adding the perfluorocarbon and optionally the metal compound to a solution of the biocompatible hydrophobic polymer in a polar solvent to provide a first liquid mixture, adding the first liquid mixture to an aqueous solution of a biocompatible surfactant including polyvinylalcohol under sonication to obtain a second liquid mixture, a) maintaining the sonication of the second liquid mixture while cooling, b)
(Continued)

evaporating the polar solvent from the second liquid mixture to obtain a suspension of beads including the biocompatible hydrophobic polymer, the perfluorocarbon and optionally the metal compound, c) separating the beads from the suspension and preparing a water suspension of the beads and d) freeze-drying the water suspension to obtain the beads, wherein the addition of the first liquid mixture to the biocompatible surfactant in step b) is performed within a period of at most 10 seconds, wherein the sonication in step b) and the sonication in step c) are performed directly into the liquid mixtures by for example a probe or flow sonicator at an amplitude of at least 120 μm for 0.01-10 minutes and wherein the weight ratio of the biocompatible surfactant to the biocompatible hydrophobic polymer is at least 3:1. Beads having close F—H2O interactions, which are suitable for imaging purposes.

13 Claims, 10 Drawing Sheets

(51) Int. Cl.
| | |
|---|---|
| *A61K 49/18* | (2006.01) |
| *A61K 49/22* | (2006.01) |
| *G01N 29/24* | (2006.01) |
| *A61K 49/00* | (2006.01) |
| *C08J 3/09* | (2006.01) |
| *G01R 33/28* | (2006.01) |
| *A61K 49/10* | (2006.01) |
| *A61K 49/12* | (2006.01) |
| *C08K 3/08* | (2006.01) |
| *C08K 5/02* | (2006.01) |

(52) U.S. Cl.
CPC ............ *A61K 49/223* (2013.01); *C08J 3/093* (2013.01); *C08J 3/095* (2013.01); *G01N 29/2418* (2013.01); *A61K 49/108* (2013.01); *A61K 49/12* (2013.01); *C08J 2329/04* (2013.01); *C08J 2467/04* (2013.01); *C08K 3/08* (2013.01); *C08K 5/02* (2013.01); *G01N 2291/02475* (2013.01); *G01R 33/281* (2013.01)

(56) References Cited

FOREIGN PATENT DOCUMENTS

| WO | 2012113733 A1 | 8/2012 |
|---|---|---|
| WO | 2014041150 A1 | 3/2014 |
| WO | 2017001686 A1 | 1/2017 |

OTHER PUBLICATIONS

Koshkina, Olga et al., "Perfluorocarbon-loaded polymeric nanoparticles for cell tracking using multimodal in vivo imaging", Abstracts of Papers, 251st ACS National Meetings & Expo, San Diego, CA, Mar. 13-17, 2016, Coll-39 Publisher: American Chemical Society, Washington DC, XP 02761621.

Fabrizio Calliada et al., "Ultrasound Contrast Agents Basic Principles", European Journal of Radiology 27, (1998) S157-S160, Elsevier Science Ireland Ltd.

Database WPI, Week 200982, Thomson Scientific, London, GB; AN 2009-R44826, XP002770335.

PROCESS FOR PREPARATION OF BEADS FOR IMAGING

FIELD OF THE INVENTION

The present invention relates to a process for the preparation of beads useful as a contrast agent in medical imaging. The invention further relates to the beads obtainable by such process and use of such beads.

BACKGROUND OF THE INVENTION

In vivo imaging techniques are essential to personalized medicine and therapies, including cell therapy. There are currently nearly 10,000 ongoing clinical trials involving some form of cell therapy (www.clinicaltrials.gov). A key hurdle in the development and optimization of cell therapy is that there are insufficient means to monitor the cells once they are in the patient, in a noninvasive manner. Other areas where imaging is essential include the optimization and monitoring of implants/matrices/scaffolds, drug delivery, targeted therapies; and monitoring disease status or response to therapy, such as in regions of inflammation, cardiovascular plaques or tumors.

Although several clinical imaging modalities are available, none are optimal. Thus, agents visible with more than one imaging modality (multimodal imaging agents) are desirable. It has been attempted to develop agents so that they could be visualized using a combination of imaging techniques, such as 1 H MRI, 19 F MRI, fluorescence imaging and acoustic imaging techniques, including ultrasound and optoacoustic imaging.

The use of ultrasound in medical imaging procedures is well known in the art. It is the most frequently used clinical imaging modality. Ultrasound is known as an economical, non-invasive, real time technique with a well-established safety record. It can be used for longitudinal studies and repeated use is not harmful for the body.

Ultrasound devices do not produce any ionizing radiation and their operation does not involve the use of radiolabels. The devices for performing ultrasound imaging are portable and already in widespread use. Ultrasound imaging is potentially quantitative and it is not a whole body imaging modality, and is therefore limited to target organs. Ultrasound imaging is limited with respect to depth of imaging.

Typically, gas-filled microbubbles are employed as contrast agents in ultrasound imaging. They commonly have a relatively large size (1000-10000 nm diameter) which is generally unsuitable for applications such as cell labeling. Moreover, they are also unsuitable for imaging outside the blood stream e.g. in tumor imaging. Such gas-filled microbubbles have a short lifetime, typically in the order of seconds to minutes. They also suffer from the additional disadvantage that cell damage, including to blood vessels, may occur as the gas bubbles burst. Moreover, gas-filled microbubbles can be unstable so that they cannot be stored for a significant amount of time; they typically have to be used soon after hydration. Finally, such large agents cannot leave the circulation and thus present very limited opportunities for in vivo targeting or drug delivery applications. Their large size also encourages prompt clearance by the kidneys, which further limits their useful lifetime in vivo.

Ultrasound contrast agents and their use are reviewed in Ultrasound contrast agents: basic principles. Eur J Radiol. 1998 May;27 Suppl 2:S157-60 and Kiessling et al., Theranostics 201 1, volume 1, 127-134.

U.S. Patent application 2010/0158815 describes the use of contrast agents that are internalized in a cell for improving the ultrasound visibility of the cell. This however has the inherent disadvantage that the agent is gaseous and unstable for cell tracking beyond a few hours. Furthermore, gaseous agents can cause cell damage, for example to the membranes or cytoskeleton.

U.S. patent application 2011/0020239 provides methods for labeling cells ex vivo for imaging applications, and does not describe in detail any particular contrast agent.

WO2012/113733 discloses nanoparticles, comprising a gadolinium compound and/or incorporated perfluorooctyl bromide, for use as contrast media in magnetic resonance tomography (MRT)-assisted diagnosis of liver diseases, more particularly of hepatocellular carcinoma (HCC).

WO2014/041150 discloses a poly(lactic-co-glycolic) acid (PLGA) particle comprising a perfluoro crown ether and a gadolinium chelate and its use for in vitro imaging and in vivo imaging. In WO2014/041150, the particles are prepared by mixing a solution of PLGA, perfluoro-15-crown-5-ether and a solution of gadoteridol, dropwise addition of the mixture into a solution of polyvinyl alcohol under sonication using a cup horn, followed by evaporation and lyophilization. While WO2014/041150 discloses PLGA particles which are stable, affordable and effective contrast agents suitable for cell imaging such as ultrasound and optoacoustic imaging techniques, there is a need in the art to further improve the process such as the yield of the particles which can be obtained by the process.

Furthermore, there is a need for particles have a narrow size distribution, and a high response in imaging.

SUMMARY OF THE INVENTION

It is an object of the present invention to provide beads useful for imaging in which the above-mentioned and/or other needs are met.

Accordingly, the present invention provides a process for the preparation of beads comprising a biocompatible hydrophobic polymer, a polyvinylalcohol, a perfluorocarbon and optionally a metal compound, comprising the steps of: a) adding the perfluorocarbon and optionally the metal compound to a solution of the biocompatible hydrophobic polymer in a polar solvent to provide a first liquid mixture, b) adding the first liquid mixture to an aqueous solution containing polyvinylalcohol (PVA) under sonication to obtain a second liquid mixture, c) maintaining the sonication of the second liquid mixture while cooling, d) evaporating the polar solvent from the second liquid mixture to obtain a suspension of beads comprising the biocompatible hydrophobic polymer, the perfluorocarbon, PVA and optionally the metal compound, e) separating the beads from the suspension and preparing a water suspension of the beads and f) freeze-drying the water suspension to obtain the beads, wherein the addition of the first liquid mixture to the biocompatible surfactant in step b) is performed within a period of at most 10 seconds, wherein the sonication in step b) and the sonication in step c) are performed directly to the liquid mixtures at an amplitude of at least 120 µm for 0.01-10 minutes and wherein the weight ratio of the biocompatible surfactant to the biocompatible hydrophobic polymer is at least 3:1.

Preferably the amplitude is at least 240 µm.

It was surprisingly found that the rapid addition of the liquid mixture of the biocompatible polymer, the perfluorocarbon and the optional metal compound to the solution of the biocompatible surfactant in combination with a high energy sonication resulted in improved yield of the beads. Further the beads contain PVA, and show a surprising F—H2O interaction.

By the rapid addition of the first liquid mixture to the solution of the biocompatible surfactant, there is essentially no difference in the duration of sonication applied to the first liquid mixture added in the beginning or at the end. In comparison, a slow addition of the first liquid mixture to a solution of a biocompatible surfactant results in the portion of the mixture added later being exposed to sonication for a shorter period of time.

Direct sonication in steps b) and c) is preferably performed by using a probe or by using a flow sonicator. The direct sonication with the use of a probe or flow sonicator as opposed to indirect sonication by for example a cup horn results in improved energy transfer. This homogeneous, high energy sonication using a probe or flow sonicator led to a good yield of beads. Further, the process resulted in beads with a narrow particle size distribution and a small average particle size. In contrast to a probe/flow sonicator, a cup horn such as used in WO2014041150 is a bath sonicator filled with cooling liquid, the temperature of which is controlled by a refrigerated circulator. Thus, during the sonication the ultrasound waves have to pass the filling liquid of the water bath and glass walls of the flask. These factors result in loss of energy and make the sonication sensitive to further parameters, e.g. inhomogenities of the flask walls, or possible deviations of movement of cooling liquid or of the height of cooling liquid. Although not wishing to be bound by any theory, it is believed that these factors lead to the differences in the yield and the properties of the beads obtained.

The beads obtained according to the invention have a good visibility in several imaging modalities. Such beads may be advantageously employed in qualitative or quantitative imaging such as acoustic imaging including optoacoustic and ultrasound imaging, MRI imaging, such as 19 F imaging, 1 H imaging including T1 and T2 weighted imaging, SPECT, PET, scintigraphy and fluorescence imaging (with addition of fluorescent dyes or radioligands). This may then be employed in cell labeling, microscopy, histology, targeted applications, drug delivery or for imaging vasculature or perfusion, including differentiating normal from abnormal vasculature, in vivo and in vitro. The beads may also be detected using fluorescence imaging or bioluminescence if either a fluorescent dye or luciferase (or nucleic acid coding for luciferase) was incorporated in the particle [Pharm Res 2004; 21:354-364].

The term "bead" is herein understood to mean a matter which is solid when dry at room temperature and which can be recovered from a sol (a dispersion of solid dispersed in a liquid continuous phase) by precipitation and lyophilization. The beads according to the invention are also stable to repeated freeze/thaw and lyophilization cycles.

Liposomes, micelles and emulsion droplets are thus not included in the term "beads" as used herein. They consist of a liquid surfactant coating (typically a lipid) over the dispersed phase, which is also a liquid for imaging applications, except in the case of microbubbles where the dispersed phase is a gas.

Hence, "perfluorocarbon nanoparticles" mentioned in publications such as Invest Radiol. 2006 March;41 (3):305-12, Radiology. 2013 August;268(2):470-80 are "perfluorocarbon emulsion droplets" and are not "beads" as used here. Emulsion droplets cannot be recovered intact by lyophilization, and emulsions are subject to flocculation, creaming, coalescence and/or Ostwald ripening. These effects do not apply to beads as used herein.

Biocompatible Hydrophobic Polymer

In step a), a solution of a biocompatible hydrophobic polymer in a polar solvent is used. It will be appreciated that the combination of the biocompatible hydrophobic polymer and the polar solvent must be selected such that the biocompatible hydrophobic polymer dissolves in the polar solvent.

The term "biocompatible" as used herein refers to a property of a material that does not cause substantially harmful response to the subject when introduced to a subject. For example, it means that when materials or devices which are foreign to a subject are used, they do not induce substantially harmful reactions such as inflammatory reaction and/or immune reactions. Biocompatible materials which may be used for the present disclosure include biodegradable or biosafety materials.

As used herein, a polymer is determined as hydrophobic when 100 mg of the polymer does not dissolve in 100 mL of water at room temperature at 1 atm.

Preferably, the biocompatible hydrophobic polymer comprises a polymer selected from the group consisting of poly(lactic-co-glycolic) acid (PLGA), poly(lactic acid) (PLA), poly(caprolactone), polydimethylsiloxane and combinations thereof. The hydrophobic polymer may be modified, for example at its end groups, to incorporate binding sites or active sites (such as "click" groups), or to incorporate active agents (such as fluorescent dyes), or additional polymers such as PEG. Particularly preferably, the biocompatible hydrophobic polymer is PLGA.

The term "poly(lactic-co-glycolic) acid" or PLGA is a term recognized in the art and means a biodegradable polymer of lactic and glycolic acid monomers of variable length and composition. PLGA beads may also comprise addition polymers such as for example poly-ethylene glycol (PEG, Curr Drug Deliv. 2004 October;1 (4):321-33). PLGA beads/particles are known in the art and have been described for use in imaging (e.g. Biomaterials. 2010 September;31 (27):7070-7). The structure of PLGA is shown in Formula 1 (x and y denote the number of units of lactic and glycolic acid respectively).

Formula 1

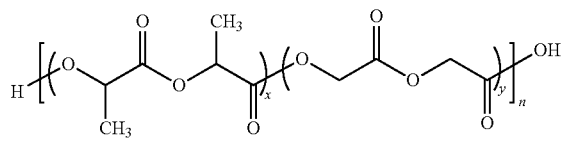

Gas-filled PLGA particles have also been suggested for use in ultrasound. Patent application CN 101574530A describes the use of a PLGA-PEG-PLGA multipolymer microbubble ultrasound contrast agent wherein the microbubble comprises a gas such as perfluoropropane, decafluorobutane or sulfur hexafluoride.

Perfluorocarbon

A perfluorocarbon is added to the solution of the biocompatible hydrophobic polymer as a liquid. The term "liquid" as used herein refers to the liquid physical state of a compound when in an isolated form at body temperature (37 degrees C.) at standard atmospheric pressure (approximately 1000 hectopascal).

The term "perfluorocarbon" refers to a carbon compound or a polymer where essentially all or all carbon-hydrogen bonds are replaced by carbon-fluorine bonds. Perfluorocarbons can include other elements, such as oxygen. Preferred perfluorocarbons include perfluoropolyethers, perfluoro crown ethers, perfluorooctane, perfluorooctylbromide and perfluoro poly ethers and combinations and modifications thereof. Particularly, preferred perfluorocarbons are perfluoro crown ethers.

The term "perfluoro crown ether" (PFCE) is to be interpreted as a cyclic perfluorocarbon containing carbon, oxygen and fluorine covalently bound in a stable ring structure.

A particularly useful perfluoro crown ether is perfluoro-15-crown-5-ether the structure of which is shown in formula 2.

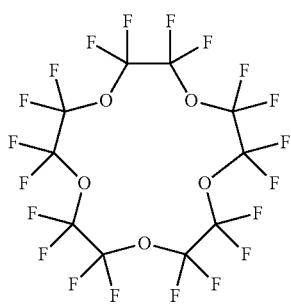

Formula 2

Metal Compound

The metal compound adds the possibly of contrast in 1 H MRI, i.e. the metal compound may serve as an MRI contrast agent.

The term "metal compound" refers to a metal per se and a compound comprising a metal such as a metal chelate. A metal is an element defined as a metal in the periodic table of elements, including transition metals, alkaline metals and rare earth metals.

A particular favorable metal compound comprises lanthanides, such as gadolinium (Gd). Gadolinium chelates are commercially available as e.g. a composition called "Prohance®" comprising gadoteridol. The structure of gadoteridol is shown in formula 3.

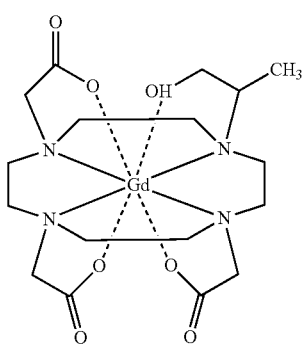

Formula 3

Step a)

Step a) involves adding a perfluorocarbon and optionally a metal compound to a solution of the biocompatible hydrophobic polymer in a polar solvent to provide a first liquid mixture. The perfluorocarbon is added as a liquid.

When step a) involves adding the metal compound to the solution of the biocompatible hydrophobic polymer, step a) is performed under direct sonication using for example a probe or flow sonicator such that the first liquid mixture is obtained as an emulsion. This leads to a narrower size distribution and a smaller average size. The skilled person can easily visually determine whether an emulsion has been obtained or not and therefore can adjust the energy (amplitude and duration of the sonication) to be applied in step a).

Preferably, the metal compound is added as a solution comprising a relatively high amount of the metal compound, for example at least 100 mg per mL of the solution, at least 200 mg per mL of the solution or at least 250 mg per mL of the solution. For example, a commercially available agent, Prohance®, is a solution comprising 279.3 mg of gadoteridol per mL of the solution. Such solution can be added without dilution. A high concentration of the metal compound to be mixed with the biocompatible hydrophobic polymer results in stable emulsion droplets, which result in higher yield and/or better size distribution.

When step a) does not involve adding the metal compound to the solution of the biocompatible hydrophobic polymer, the first liquid mixture obtained is a multi-phase system comprising a phase of the perfluorocarbon and a phase of the solution of the biocompatible hydrophobic polymer.

Preferably, the polar solvent of the solution of the biocompatible hydrophobic polymer is an organic solvent and is selected from the group consisting of dichloromethane (DCM), chloroform, ethyl acetate and combinations thereof. Due to its low boiling point, which makes evaporation at the room temperature possible, the use of DCM is preferable.

Preferably, the weight ratio of the perfluorocarbon in the first liquid mixture with respect to the biocompatible hydrophobic polymer in the first liquid mixture is between 10:1 to 25:1, for example between 12:1 to 20:1, for example between 14:1 to 18:1.

Preferably, the weight ratio of the metal compound in the first liquid mixture with respect to the biocompatible hydrophobic polymer in the first liquid mixture is between 1:1000 to 1:100, for example between 1:500 to 1:150, for example between 1:300 to 1:180.

Step b)

Step b) involves adding the first liquid mixture to an aqueous solution of PVA and optionally other biocompatible surfactants under sonication to obtain a second liquid mixture. The second liquid mixture is an emulsion.

PVA is applied as a biocompatible surfactant. The second liquid mixture may also contain other surfactants selected for example from the group consisting of a polysorbate and polyvinylpyrrolidone and combinations thereof. The polysorbate may e.g. be polysorbate 20 or polysorbate 80. Particularly preferably, the biocompatible surfactant is PVA.

The addition of the first liquid mixture to the biocompatible surfactant solution in step b) is performed within a period of at most 10 seconds, for example between 1-8 seconds or between 3-6 seconds.

The direct sonication takes place directly into the mixture containing the components for making the beads according to the invention. Preferably, a probe or a flow sonicator are being used to apply sonication to the mixture of components. The application time can vary depending on the system used and is generally between 0.01 minute and 10 minutes. When a probe is being used, the times are typically between 1 and 10 minutes. When a flow sonicator is being used, the times may be shorter for example between 0.01 and 5 minutes.

A probe is inserted into the mixture for sonication and provides a direct sonication to the mixture, in contrast to an indirect sonication provided e.g. by a Cup Horn or a Microplate Horn. The probe may also be referred as a microtip or a microtip probe and has a relatively small diameter such as 3-7 mm, for example 3 mm, 3.2 mm, 5 mm, 6 mm and 6.5 mm. Most preferably, the probe has a diameter of 3 mm or 3.2 mm (⅛ inch) for its very high intensity. Alternatively, this direct sonication could also be performed in a flow sonication cell, which is also in direct contact with a liquid.

Probes suitable for step b) are suitable for step a) and step c). Same types of probes may be used for steps b) and c), or b), c) and a). It is also possible to use different types of probes between steps b), c) and a). From practical point of view, the same probe is used for steps b) and c).

The sonication in step b) and the sonication in step c) are performed for example by a probe at an amplitude of at least 120 μm, preferably of at least 240 μm for 0.01-10 minutes. The amplitude is the distance of one movement of the probe from peak to peak during sonication and is the measure of the intensity of the sonication. The desired amplitude may be achieved by adjusting the percentage of the setting depending on the probe diameter. For example, an amplitude of 240 μm may e.g. be achieved by setting the sonicator at about 30% for a probe having a diameter of 3.2 mm. At such setting, the total energy applied to the second liquid mixture in steps b) and c) may be about 2700 J in 3 minutes. An amplitude of 300 μm may e.g. be achieved by setting the sonicator at about 40% for a probe having a diameter of 3.2 mm. At such setting, the total energy applied to the second liquid mixture in steps b) and c) may be about 4140 J in 3 minutes. When the probe has a larger diameter, the setting of the sonicator may be set to a higher percentage for achieving the same amplitude. The sonication is typically performed at a frequency of 16-24 kHz, for example 20 kHz.

Preferably, the duration of the sonication in step b) and step c) is between 2-6 minutes, for example between 2.5-5 minutes.

Preferably, the amplitude of the sonication in step b) and step c) is between 250-500 μm, for example between 270-400 μm, for example between 290-350 μm.

Particularly preferably, the sonication in step b) and the sonication in step c) are performed by a probe at an amplitude of between 290-350 μm for 2.5-5 minutes.

Preferably, the aqueous solution of the biocompatible surfactant has a concentration of 0.5-3.0 wt. %, for example 1-2.5 wt. %, for example 1.5-2.0 wt. %.

The weight ratio of the biocompatible surfactant with respect to the biocompatible hydrophobic polymer is between 3:1 to 10:1, for example between 4:1 to 8:1 or between 5:1 to 6:1. It is particularly preferred that the weight ratio of the biocompatible surfactant with respect to the biocompatible hydrophobic polymer is at least 4:1, which leads to a smaller particle size and a narrower particle size distribution.

step c)

Step c) involves maintaining the sonication of the second liquid mixture while cooling, such as by placing a container containing the second liquid mixture in an ice-water bath.

step d)

Step d) involves evaporating the polar solvent from the second liquid mixture obtained by step c) to obtain a suspension of beads.

This may be performed e.g. at a temperature within 3° C. to room temperature, preferably while stirring. The duration of the evaporation may e.g. be 6-24 hours. After the evaporation of the polar solvent, beads comprising PLGA, PFCE and optionally the metal compound precipitate and a suspension of the beads is obtained.

step e)

Step e) involves separating the beads obtained by step d) from the suspension and preparing a water suspension of the beads.

The separation may be performed e.g. by centrifugation. The acceleration and the duration of the centrifugation may be suitably selected by the skilled person. For example, the centrifugation may be carried out at e.g. at 15000-30000 g (e.g. 16087 g or 27200 g) for e.g. 15-60 minutes (e.g. 30-40 minutes).

The separated beads are resuspended in a suitable amount of water. The beads obtained by step d) are thus washed. The resuspension may be done by sonication, including bath sonication or other techniques.

The separation and resuspension step may be repeated as desired.

step f)

Step f) involves freeze-drying the water suspension obtained by step e) to obtain the beads according to the invention. Freeze-drying may be performed as well-known in the art using liquid N2 or another freezing systems with max temperature of −50° C. during the freezing phase.

Preferably, the process according to the invention results in at least 1 mg of the beads per 1 mg of the biocompatible hydrophobic polymer used in step a). More preferably, the process according to the invention results in at least 1.2 mg, at least 1.5 mg or at least 1.8 mg of the beads per 1 mg of the biocompatible hydrophobic polymer used in step a).

a) In some preferred embodiments, the invention provides a process for the preparation of beads comprising a polymer selected from the group consisting of poly(lactic-co-glycolic) acid, poly(lactic acid), poly(caprolactone), polydimethylsiloxane and combinations thereof, a perfluorocarbon and optionally a metal compound, comprising the steps of: a) adding the perfluorocarbon and optionally the metal compound to a solution of the polymer (preferably PLGA) in a polar solvent to provide a first liquid mixture, b) adding the first liquid mixture to an aqueous solution of a biocompatible surfactant polyvinylalcohol and optionally an additional surfactant selected from the group consisting of a polysorbate or polyvinylpyrrolidone under sonication to obtain a second liquid mixture, c) maintaining the sonication of the second liquid mixture while cooling, d) evaporating the polar solvent from the second liquid mixture to obtain a suspension of beads comprising the polymer (preferably PLGA), the perfluorocarbon and optionally the metal compound, e) separating the beads from the suspension and preparing a water suspension of the beads and f) freeze-drying the water suspension to obtain the beads, wherein the addition of the first liquid mixture to the biocompatible surfactant in step b) is performed within a period of at most 10 seconds, wherein the sonication in step b) and the sonication in step c) are performed directly in the liquid mixture by a probe at an amplitude of at least 120 μm for 1-10 minutes and wherein the weight ratio of the biocompatible surfactant to the polymer (preferably PLGA) is at least 3:1.

Sonication is preferably performed at an amplitude of at least 240 μm.

The process according to the invention may be performed batch-wise. Alternatively, the process according to the invention may be performed in a continuous (micro-)flow process. In a continuous process direct sonication can be carried out in a flow sonicator cell.

Beads

The invention also relates to the beads obtainable or obtained by the process according to the invention.

The present invention also provides use of the process according to the invention for preparing beads which have a homogeneous multi-domain structure, the beads comprising a biocompatible hydrophobic polymer, a perfluorocarbon, at least 10 wt. % of polyvinylalcohol and optionally a metal compound.

The present invention also provides beads, which have a homogeneous multi-domain structure, the beads comprising a biocompatible hydrophobic polymer, a perfluorocarbon and optionally a metal compound.

According to another aspect, the present invention provides beads comprising a biocompatible hydrophobic polymer, a perfluorocarbon, PVA and optionally a metal compound, wherein the beads show spin-lattice relaxation times as measured by solid state nuclear magnetic resonance (NMR) at 10 kHz MAS at 850 MHz spectrometer of T1D at a dry state and T1W at a water-swollen state, wherein T1D-T1W at 25° C. is at least 0.05 second, and/or
T1D-T1W at 15° C. is at least 0.05 second and/or
T1D-T1W at 5° C. is at least 0.05 second and/or
T1D-T1W at −5° C. is at least 0.05 second and/or
T1D-T1W at −15° C. is at least 0.05 second and/or
T1D-T1W at −25° C. is at least 0.05 second.

Beads in a dry state are understood as the freeze-dried beads obtained after step f). Beads in a water-swollen state are understood as the beads which are immersed in water for 10 minutes and subjected to centrifugation of 21000 g.

The beads according to the invention may show spin-spin relaxation times as measured by solid state nuclear magnetic resonance (NMR) at 10 kHz MAS at 850 MHz spectrometer of T2D at a dry state and T2W at a water-swollen state, wherein T2W-T2D at 25° C. is at least 0.05 second, and/or
T2W-T2D at 20° C. is at least 0.05 second, and/or
T2W-T2D at 15° C. is at least 0.05 second and/or
T2W-T2D at 5° C. is at least 0.05 second and/or
T2W-T2D at −5° C. is at least 0.03 second and/or
T2W-T2D at −15° C. is at least 0.05 second and/or
T2W-T2D at −25° C. is at least 0.01 second.

Preferably, in two dimensional heteronuclear 1H-19F NMR measurement, the beads according to the invention which do not comprise the metal compound show a Heteronuclear Overhauser Enhancement between a peak at 4.7 ppm of 1H and a peak at −92 ppm of 19F.

The beads according to the invention comprise a biocompatible hydrophobic polymer, preferably selected from the group consisting of poly(lactic-co-glycolic) acid (PLGA), poly(lactic acid) (PLA), poly(caprolactone), polydimethylsiloxane and combinations thereof.

Most preferably, the biocompatible polymer comprises PLGA. The amount of biocompatible polymer ranges preferably between 2 and 10 wt. %, more preferably between 3 and 8 wt %, relative to the weight of the beads.

The beads according to the invention comprise polyvinylalcohol as biocompatible surfactant. The presence of the biocompatible surfactant in the beads may be determined e.g. by thermogravimetric analysis or 1H-NMR. The amount of PVA in the beads according to the invention may be 8-40 wt. %, preferably between 10 and 35 wt. %, or between 11 and 30 wt. %, relative to the weight of the beads. The amount of the biocompatible surfactant in the beads may e.g. be determined by a colorimetric method as described in Journal of Controlled Release 82 (2002) 105-114.

Preferably the amount of PVA is determined according to 1H-NMR. The PVA can have different molecular weights. For example Mw can range between 5000 and 500000. Preferably the Mw ranges between 6000 and 20000, or between 7000 and 15000 Daltons.

PVA can have a degree of hydrolysis between 60 and 99%, preferably between 70 and 90%.

Preferably, the beads according to the invention have a peak radius of at most 200 nm and PDI of at most 0.2, as determined by dynamic light scattering (DLS).

Preferably, the beads according to the invention have a peak radius of at most 150 nm, or 140 nm, more preferably between 90 and 130 nm, as determined by dynamic light scattering (DLS).

Preferably, the beads according to the invention have PDI of at most 0.15 or 0.14, more preferably at most 0.13, more preferably at most 0.10, as determined by dynamic light scattering (DLS).

Preferably, the amount of the perfluorocarbon (preferably PFCE) in the beads according to the invention is at least 15% by weight, more preferably at least 20% by weight, for example 25-50 wt % with respect to the beads. Higher perfluorocarbon content is more beneficial for imaging sensitivity.

The beads according to the invention have a homogeneous structure (see FIGS. 1-5), as opposed to a core-shell structure as has been described for other agents in the literature including prior art on PLGA-perfluorocarbon nanocapsules (IEEE Trans Ultrason Ferroelectr Freq Control. 2014 January;61(1):5-15, High-frequency (20 to 40 MHz) acoustic response of liquid-filled nanocapsules), or perfluorocarbon emulsion droplets, or even phase-change perfluorocarbon droplets and microbubbles. This unique structure with multiple perfluorocarbon domains that are distributed in the polymeric matrix allows for distinct possibilities particularly with respect to ultrasound imaging, optoacoustic imaging and further applications such as delivery or therapeutic agents.

Additional Components in Beads

The beads according to the invention may comprise further components for allowing use of the beads for desired imaging purpose.

For example, the beads according to the invention may comprise a targeting agent for in vivo application or to enhance cell labeling. The term "targeting agent" refers herein to an agent that directs the beads to a relevant site or to a particular cell or cell type in vivo or in vitro. Particular advantageous targeting agents include antibodies, nanobodies and receptor ligands.

The beads according to the invention may comprise a fluorescent agent, such as a fluorescent dye, quantum dot, carbon dot, graphene dot or a fluorescent protein or nucleic acid coding for a fluorescent agent. This allows the fluorescence imaging of the beads, including in vivo, as well as histological or other microscopic analyses.

The beads according to the invention may comprise a radionuclide. That allows for autoradiography, scintigraphy, SPECT, PET or other detection methods that can detect radioactive compounds. Also, by incorporating the luciferase enzyme or nucleic acid vector coding for luciferase (or related enzymes), bioluminescence can be used for detection in vivo.

The beads may also be coated with additional agents to modify biocompatibility, such as with a PEG or modified-PEG coating.

Components necessary for use of the beads according to the invention for particular imaging purpose are known.

These components may be added in a suitable form in step a) such that the first liquid mixture contains the desired additional components, or in step b) such that the second liquid mixture contains the desired additional components. A few agents may be added as coatings to the beads, such as for targeting purposes.

Use of Beads

The invention relates to use of the beads according to the invention for in vitro imaging selected from the group consisting of acoustic imaging; optoacoustic imaging; ultrasound imaging; endoscopic or intra-operative imaging; spectroscopic techniques including Raman spectroscopy; magnetic resonance imaging or spectroscopy techniques such as 1H or 19F MRI or NMR or MRS; T1, T2 and T2* weighted imaging; proton or 19F density weighted imaging; SPECT; PET; scintigraphy; bioluminescence imaging and fluorescence imaging tomography.

The invention further relates to the beads according to the invention for use in in vitro imaging selected from the group consisting of acoustic imaging; optoacoustic imaging; ultrasound imaging; endoscopic or intra-operative imaging; spectroscopic techniques including Raman spectroscopy; magnetic resonance imaging or spectroscopy techniques such as 1H or 19F MRI or NMR or MRS; T1, T2 and T2* weighted imaging; proton or 19F density weighted imaging; SPECT; PET; scintigraphy; bioluminescence imaging and fluorescence imaging tomography.

The in vitro imaging may be for the purpose of diagnostic imaging, anatomic imaging, imaging of metastases and vasculature, quantitative imaging, qualitative imaging, therapeutic imaging, imaging of cellular transplants, imaging of cellular therapeutics, in vitro cell labeling, in vitro microscopy or in vitro histology.

The invention relates to use of the beads according to the invention for in vivo imaging selected from the group consisting of acoustic imaging; optoacoustic imaging; ultrasound imaging; endoscopic or intra-operative imaging; spectroscopic techniques including Raman spectroscopy; magnetic resonance imaging or spectroscopy techniques such as 1 H or 19F MRI or NMR or MRS; T1, T2 and T2* weighted imaging; proton or 19F density weighted imaging; SPECT; PET; scintigraphy; bioluminescence imaging and fluorescence imaging tomography.

The invention further relates to the beads according to the invention for use in in vivo imaging selected from the group consisting of acoustic imaging; optoacoustic imaging; ultrasound imaging; endoscopic or intra-operative imaging; spectroscopic techniques including Raman spectroscopy; magnetic resonance imaging or spectroscopy techniques such as 1H or 19F MRI or NMR or MRS; T1, T2 and T2* weighted imaging; proton or 19F density weighted imaging; SPECT; PET; scintigraphy; bioluminescence imaging and fluorescence imaging tomography.

The in vivo imaging may be for the purpose of diagnostic imaging, anatomic imaging, imaging of metastases and vasculature, quantitative imaging, qualitative imaging, therapeutic imaging, imaging of cellular transplants, imaging of cellular therapeutics, in vivo cell labeling, in vivo microscopy or in vivo histology.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

BRIEF DESCRIPTION OF THE DRAWINGS

FIG. 4 shows spin-lattice relaxation time T1 measured by solid state NMR (10 kHz MAS). There are differences in the spin-lattice relaxation time between the dry nanoparticles indicated by circles and the nanoparticles swollen with water indicated by squares. This shows that water can freely enter the entire structure, again indicating a homogeneous structure that contains small sized perfluorocarbon domains, which are distributed between polymeric chains.

FIG. 5 shows spin-spin relaxation time T2 measured at solid state NMR (10 kHz MAS). There are differences in the spin-lattice relaxation time between the dry nanoparticles indicated by green circles and the nanoparticles swollen with water indicated by blue squares.

FIG. 7 shows X-ray diffraction results of the beads comprising PLGA, PFCE and gadoteridol (line with lower intensity) and the beads comprising PLGA without PFCE and gadoteridol (line with higher intensity). The results are similar.

DETAILED DESCRIPTION OF THE INVENTION

Figure 1:
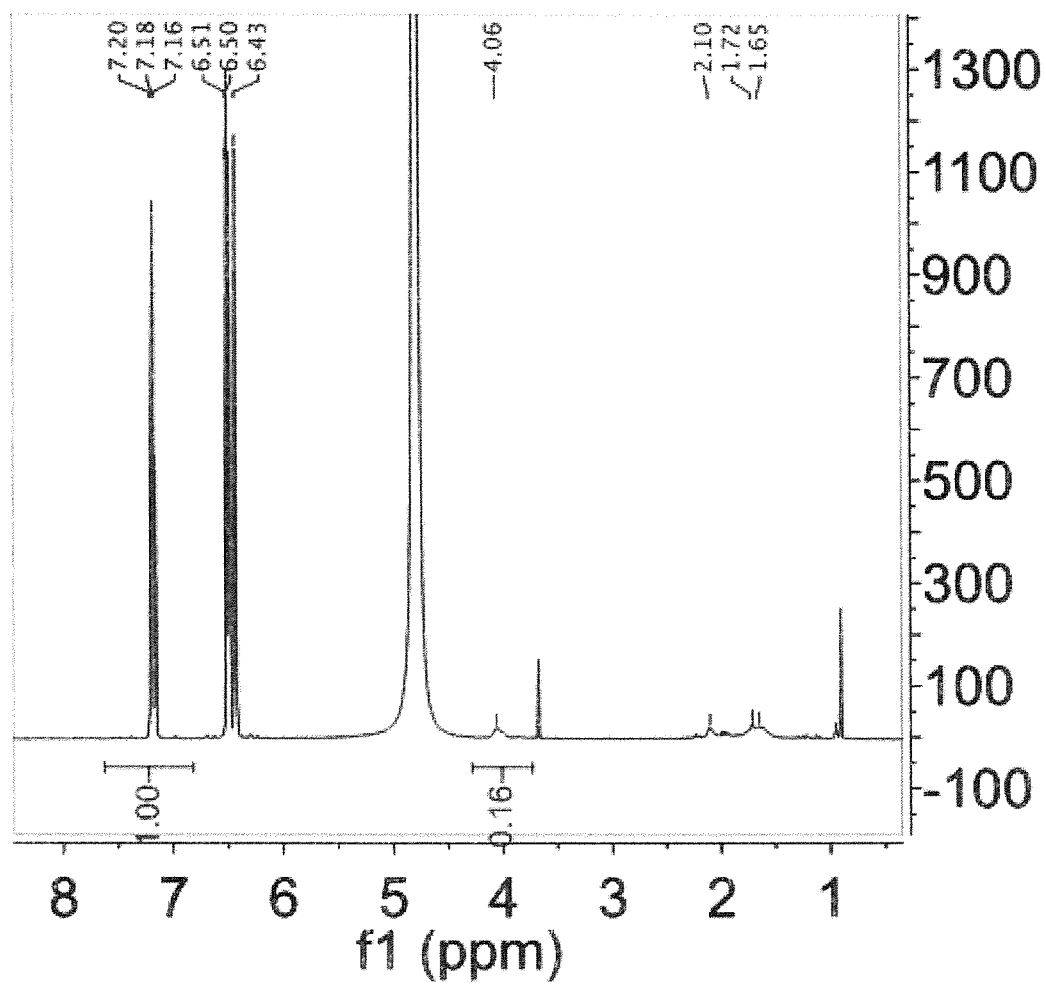
FIG. 1 shows 1H NMR spectra of particles produced by the process of WO2014/041150 (left) and new (right) process. The spectra were measured with resorcinol (4.1 mg) as an internal reference; 400 MHz, $D_2O$, relaxation decay=20 s. Inset in the right spectrum: chemical structure of PVA, non-hydrolyzed OH groups not shown for simplification.
Figure 1:
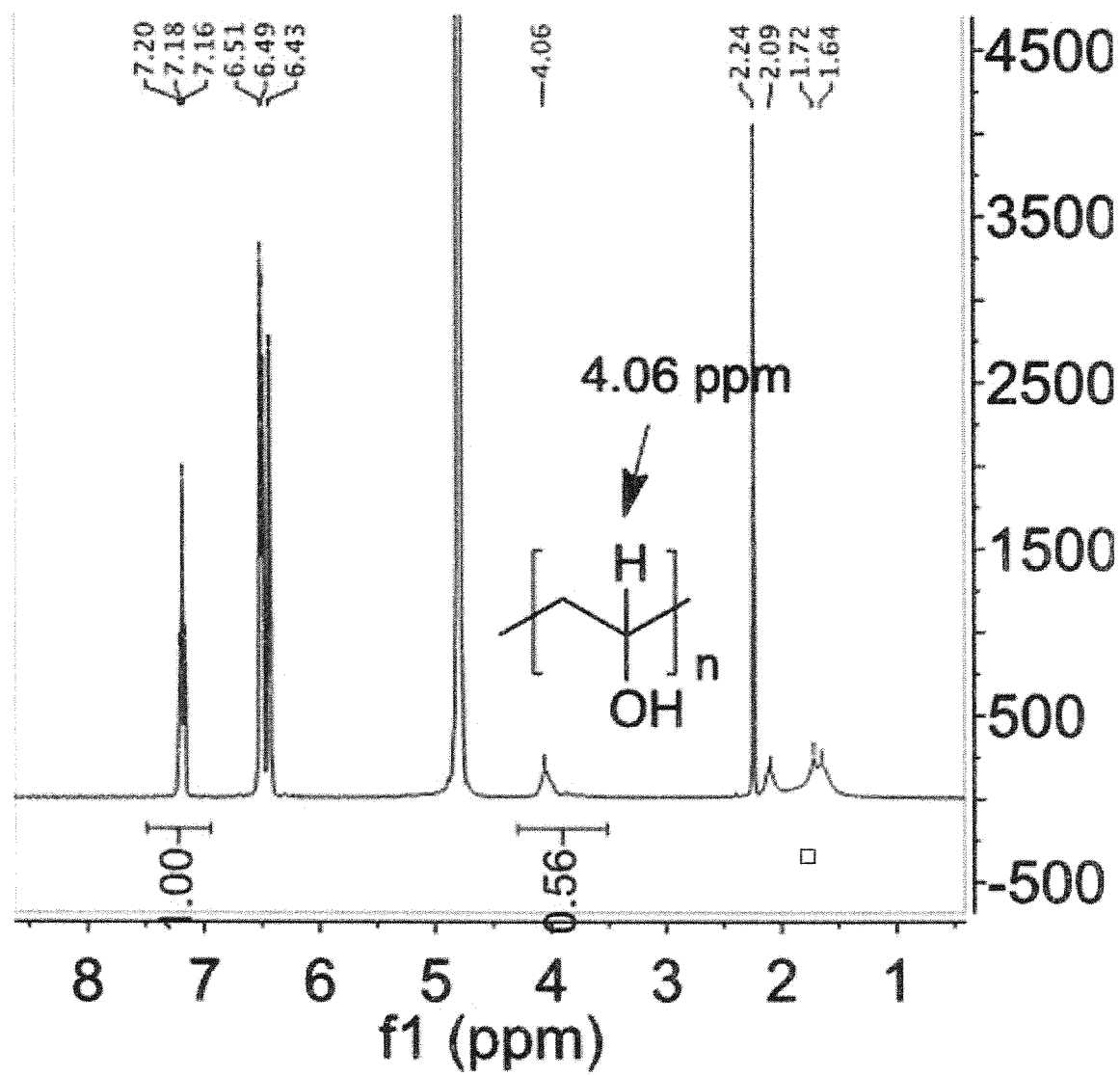

The invention is now elucidated by way of the following examples, without however being limited thereto.

EXAMPLES

Experiments 1-6: Preparation of Beads Comprising a Metal Compound

PLGA (100 mg, resomer 502H) was dissolved in 3 mL dichloromethane. Perfluoro-15-crown-5 ether (900 μL, 1600 mg) and Prohance (1.78 mL, 497 mg gadoteridol) were added to the solution of PLGA and a first emulsion was formed by sonication using a microtip having a tip diameter of 3 mm at an amplitude of 40% for 15 seconds (Digital Sonifier s250 from Branson). This first emulsion was rapidly (within 10 seconds) added to a solution of poly(vinyl alcohol) (9000-10000 Da Mw and 80% hydrolysis) (25 g of water and 100-500 mg of PVA) in a round bottom flask while sonication of PVA-containing flask was started. The entire mixture was sonicated in ice-water bath using a microtip having a tip diameter of 3 mm at an amplitude of 20% or 40% to obtain a second emulsion. A sonication setting of 20% refers to an amplitude of about 160 μm, while a sonication setting of 40% relates to an amplitude of ca 300 μm.

The duration of the period from the addition of the first emulsion to the end of the sonication was 3 minutes (Digital Sonifier s250 from Branson).

After sonication dichloromethane was evaporated at 4° C. or room temperature overnight under stirring to achieve solidification of the beads. The beads were isolated by centrifugation at 27200 g for 20 min in 50 mL centrifugation tubes and resuspended in 25 g of water. The washing step was repeated two more times with resuspention by sonication after second washing (sonication bath, Diagenode Bioruptor). After washing, beads were resuspended in 4 mL of water, frozen with liquid $N_2$ and freeze-dried. The resulting product was a white powder.

The amounts of the components and the sonication amplitude which were varied are shown in Table 1, together with the properties and the yield of the beads.

TABLE 1

| Exp. No | PVA/ mg | Sonication Amplitude | Radius (DLS; intensity)/nm | PDI | PFCE-content/ wt.-% | yield/ mg |
|---|---|---|---|---|---|---|
| 1 | 100 | 20% | 357 | 0.49 | 11 | 77 |
| 2 | 500 | 20% | 121 | 0.1 | 5.3 | 55 |
| 3 | 100 | 40% | 314 | 0.39 | 28 | 137 |
| 4 | 200 | 40% | 174 | 0.2 | 34 | 189 |
| 5 | 350 | 40% | 146 | 0.15 | 39 | 184 |
| 6 | 500 | 40% | 121 | 0.123 | 45 | 204 |

Small beads with narrow particle size distribution were obtained by the process according to the invention (Ex 4, 5 and 6). It can be observed that a high amplitude (40%) and a large amount of PVA (200 mg (8.3 wt. %), 350 mg (13.7 wt. %) or 500 mg (18.5 wt. %)) resulted in a desirable combination of a small radius, low PDI, a high PFCE content and a high yield.

Experiments 7-9: Preparation of Beads Without a Metal Compound

PLGA (100 mg, resomer 502 H) was dissolved in 3 mL dichloromethane (DCM) followed by addition of perfluoro-15-crown-5 ether (900 μL). The resulting double phase liquid was rapidly added with a glass pipette to a solution of poly(vinyl alcohol) (25 g of water and 100-500 mg of PVA) in a round bottom flask while sonication was started. Care was taken so that the phase of PLGA/DCM and the phase of PFCE were added simultaneously at a constant ratio. The entire mixture was sonicated in ice-water bath using a microtip having a tip diameter of 3 mm at an amplitude of 20% or 40% to obtain an emulsion. The duration of the period from the addition of the double phase liquid to the end of the sonication was 3 minutes (Digital Sonifier s250 from Branson).

After sonication dichloromethane was evaporated at 4° C. or room temperature overnight under stirring to achieve solidification of the beads. The beads were isolated by centrifugation at 27200 g for 35 min in 50 mL centrifugation tubes and resuspended in 25 g of water. The washing step was repeated two more times with resuspention by sonication after second washing (sonication bath, Diagenode Bioruptor). After washing, beads were resuspended in 4 mL of water, frozen with liquid $N_2$ and freeze-dried. The resulting product was a white powder with a yield of at least 100 mg.

TABLE 2

| Exp. No | PVA/ mg | Sonication Amplitude | Radius (DLS; intensity/nm | PDI | PFCE-content/ wt.-% | yield/ mg |
|---|---|---|---|---|---|---|
| 7 | 100 | 20% | 354 | 0.25 | 15 | 86 |
| 8 | 100 | 40% | 339 | 0.24 | 25 | 116 |
| 9 | 500 | 40% | 100 | 0.04 | 48 | 154 |

Small beads with narrow particle size distribution and a high PFCE content were obtained with a high yield according to the process of the invention (Ex 9).

Experiments 10-12 (Comparative)

Experiment 6 was repeated except that the PLGA was dissolved in a solvent indicated in Table 3.

TABLE 3

| Exp. No | Solvent | PVA/ mg | Sonication Amplitude | Radius (DLS; intensity)/nm | PDI | PFEC-content/ wt.-% | yield/ mg |
|---|---|---|---|---|---|---|---|
| 10 | THF | 500 | 40% | 171 | 0.5 | 15 | 131 |
| 11 | Acetone | 500 | 40% | 294 | 0.66 | 8 | 90 |
| 12 | Acetonitrile | 500 | 40% | 223 | 0.22 | 5 | 95 |

Beads obtained are larger and have a broader size distribution than the experiments in which the solvent was dichloromethane.

Diameter of beads prepared according to examples 1-12 was determined using dynamic light scattering (DLS) as described in Biomaterials. 2010 September; 31 (27):7070-7.

Experiment 13 (Comparative): Preparation of Beads Using Cup Horn

PLGA (90 mg, resomer 502 H) was dissolved in 3 mL dichloromethane. Perfluoro-15-crown-5 ether (890 µL) was added to the solution of PLGA. 50 mL of an aqueous solution comprising of Prohance with concentration of 3 mg/mL was further added. This mixture was added dropwise to a solution of poly(vinyl alcohol) (20 g/L) in a glass tube while sonication of PVA-containing flask was started. The entire mixture was sonicated in a cup horn at an amplitude of 30% for 3 minutes, with 60 s on and 10 s off cycles (Digital Sonifier s250 from Branson) to obtain a second emulsion. During the sonication the temperature of the cooling water was maintained at 4° C. by a refrigerated circulator.

After sonication dichloromethane was evaporated at 4° C. overnight under stirring to achieve solidification of the beads. The beads were isolated by centrifugation at 21000 g for 30 min in 2 mL centrifugation tubes and resuspended in 25 g of water. The pellet was washed with water twice and then resuspended in water, frozen at −80° C. and freeze-dried. The resulting product was a white powder with a yield of 50 mg.

The examples according to the invention (Ex 5, 6, 9) resulted in a much higher yield compared to experiment 13.

Experiment 14 (Comparative); Use of Other Surfactants (No PVA)

To study whether PVA is necessary for the formation of the particles of the invention, we tested the production with other surfactants that are commonly used for production of empty PLGA particles without perfluorocarbon (table 4). However, with all these surfactant we observed strong increase in size and polydispersity of nanoparticles. Especially, the PDI values, which are all higher than 0.5, demonstrate the very broad size distribution of the samples. Moreover, the encapsulation of PFCE was significantly lower or even not measurable with NMR. In summary the synthesis of nanoparticles was not possible with other surfactants. Therefore, we conclude that PVA is essential for stabilization of nanoparticles and for encapsulation of PFCE.

TABLE 4

Production of nanoparticles with different surfactants.

| Surfactant | $R_h$/nm | PDI | PFCE-content/wt.-% |
|---|---|---|---|
| Tween 20 | 215 | 0.81 | n/a |
| Sodium cholate | 390 | 0.85 | 6 |
| poly (vinylpyrrolidone) | 450 | 0.77 | 3 |
| Pluronic F68 | 315 | 0.45 | n/a |

TEST METHODS

Quantification of PFCE

PFCE content was measured with 19F NMR at Bruker Avance III 400 MHz spectrometer using D2O (sigma-aldrich) as solvent and trifluoroacetic acid as an internal reference. The relaxation delay D1 was set to 20 s. Data evaluation was done with MestreNova 10.0 from Mestrelab.

2D Heteronuclear Overhauser Enhancement Spectroscopy

HOESY of PFCE-particles were measured was measured in D2O as solvent at Bruker DMX 500 MHz NMR spectrometer with relaxation delay D1=2.0 s and cross-relaxation delay D8=0.25 s, 471 MHz ($^{19}$F), 500 MHz ($^1$H)

HOESY of PFCE-loaded core-shell capsules were performed at Bruker Avance III 400 MHz spectrometer with D1=2.0 s and D8=0.15 s, 377 MHz ($^{19}$F), 400 MHz ($^1$H).

Data evaluation was done with MestreNova 10.0 from Mestrelab.

Quantification of PVA

Concentration of PVA was measured with 1 H NMR using resorcinol as an internal reference at Bruker Avance III 400 MHz spectrometer with D2O as solvent. Relaxation delay D1=30 s. Data evaluation was done with MestreNova 10.0 from Mestrelab.

Solid State NMR

Solid state NMR was measured at Varian VNMRS 850 MHz spectrometer at 10 kHz MAS. For measuring the particles in dry state we used freeze-dried nanoparticle powder, which was obtained according to the method described in this patent. To obtain nanoparticles that are swollen with water, freeze-dried powder was incubated with excess of water for 5 min and then centrifuged at 15000 rpm using hettich micro 200 R centrifuge. The pellet from centrifugation was then immediately filled into a rotor for solid state NMR measurements. Data evaluation was performed with MatNMR.

Differential Scanning Calorimetry (DSC)

DSC was measured at Mettler Toledo DSC822e calorimeter equipped with an FRS5 sensor, a Julabo FT900 immersion cooler, a TSO 801RO Sample Robot with heating rate 2 K/min under nitrogen atmosphere using STARe software 11.0 form measurements and data analysis.

Thermogravimetric Analysis (TGA)

TGA was measured at Mettler Toledo TGA/SDTA851e instrument under nitrogen atmosphere with a heating rate of 20 K/min.

Dynamic Light Scattering (DLS)

DLS was performed at zetasizer ZS nano from Malvern instruments at sample concentration of 0.1 mg/mL in deionized water.

Small Angle X-ray Scattering (SAXS)

SAXS measurements were performed at Ganesha X-ray instrument equipped with a GeniX-Cu ultra low divergence source (I=1.54 Å, flux of 1×108 ph/s), a Pilatus 300 K silicon pixel detector (487×619 pixels of 172×172 µm2), Linkam temperature controller (−80-250° C.), Julabo temperature controller (−5-80° C.), q-range 0.003-3 Å$^{-1}$.

X-ray Diffraction (XRD)

Diffractogram was measured on a Panalytical Empyrean in reflection mode with fine-focus sealed tube, and PIXcel3D detector, using CuKα radiation. The scan range was from 2 to 50 degrees 2-theta, with a step size of 0.013 degrees.

Characterization

The beads obtained according to the process of the invention were characterized by various methods.

The particles prepared in exp 13, which is an experiment from WO2014/041150, are comprised of PLGA, PFCE and Gd-chelate. In contrast, to these particles the new beads (see experiments 1-6) contain poly(vinyl alcohol) (PVA) that was used as stabilizer during the emulsification process to facilitate the formation of stable and monodisperse particles.

Figure 2:
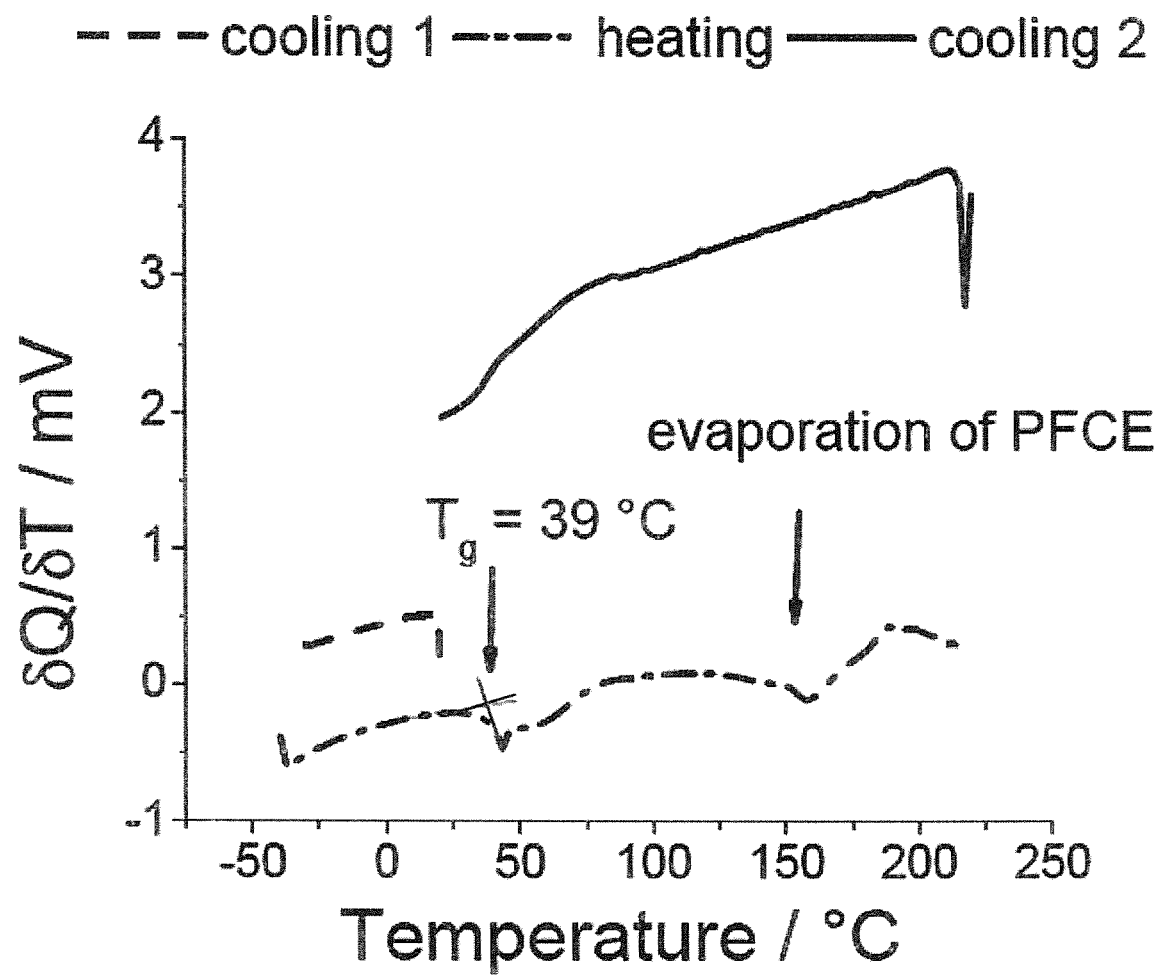
FIG. 2 shows the DSC curves measured on beads comprising PLGA, PFCE and gadoteridol according to the invention. No melting of PFCE at −17° C. and no crystallization at −19° C. can be detected indicating that PFCE phase does not have a distinct melting point. Heating rate 2 K/min, sample initial weight 10.3 mg, sample final weight 5.6 mg.

Thus, the process according to the present invention results in particles with a different composition then the process according to WO2014/041150. This changing of particle composition can be demonstrated by $^1$H NMR measurements. FIG. 2 shows quantitative $^1$H NMR spectra of particles form the old patent and the new particles with resorcinol as an internal reference. Due to reduced mobility of PLGA chains after particle formation, PLGA cannot be detected by NMR, and only signals of resorcinol and PVA are visible on both spectra.

1H NMR spectra of particles produced by the process of WO2014/041150 (left) and new (right) process have been measured (see FIG. 1). The spectra were measured with resorcinol (4.1 mg) as an internal reference; 400 MHz, D$_2$O, relaxation decay=20 s. Inset in the right spectrum: chemical structure of PVA, non-hydrolyzed OH groups not shown for simplification.

The peak at 4.06 ppm corresponds a proton of H—COH group of a monomer repeat unit, as shown on the inset in FIG. 1 right. Using the integral of the triplet signal of resorcinol at 7.18, the integral of the PVA peak at 4.06 ppm and the average molecular weight of PVA 9500 g/mol (molecular weight by manufacturer 9000-10000 g/mol) can be calculated resulting in following PVA content:

particles from the process of WO2014/041150: 7 wt.-%
particles from the new process: 23 wt.-%
Solid state NMR measurements and 2D solution NMR that are shown in the description demonstrated that PFCE interacts with water. As PLGA is a hydrophobic polymer that is not soluble in water while PVA is a hydrophilic polymer, we assume that PVA that is present in new particles promoted this interaction between PFCE and water resulting in a unique structure. PFCE is an ultrahydrophobic compound that usually does not mix with water. Thus, particles or emulsions reported until now in the literature typically have a core-shell structure.

Experiment 15 (Comparative)

To prove the unique structure of our particles, we prepared core-shell capsules as an additional control. To make these core-shell capsules, we used the procedure for synthesis PFOB-loaded capsules with sodium cholate as surfactant that was previously described by Pisani et al (Adv. Funct. Mater. 2008, 18, 2963-2971). In this procedure we replaced PFOB by 0.9 mL PFCE, to make PFCE capsules, which can then be directly compared to our PFCE beads.

PLGA (100 mg, resomer 502 H) was dissolved in 3 mL dichloromethane and mixed with perfluoro-15-crown-5 ether (900 µL) or perfluorooctylbromide (PFOB, 275 µL) by pipetting it up and down with a glass pipette. The resulting primary emulsion was added to 1.5 wt.-% solution of sodium cholate and sonicated on ice for 3 min at amplitude of 40% (branson digital sonifier s250). After sonication dichloromethane was evaporated over night under stirring at room temperature. To exchange the surfactant, PVA solution (10 g of 1.96 wt.-%) was added to the suspension and the mixture was stirred at 4° C. for 5 d. The emulsions were washed 2 times (with water at 16000 g, resuspended in 4 mL of water on a shaker at 4° C., frozen with liquid N2 and freeze-dried.

The synthesis yielded freeze-dried capsules, with R$_h$=62 nm and PDI 0.09.

Figure 3:
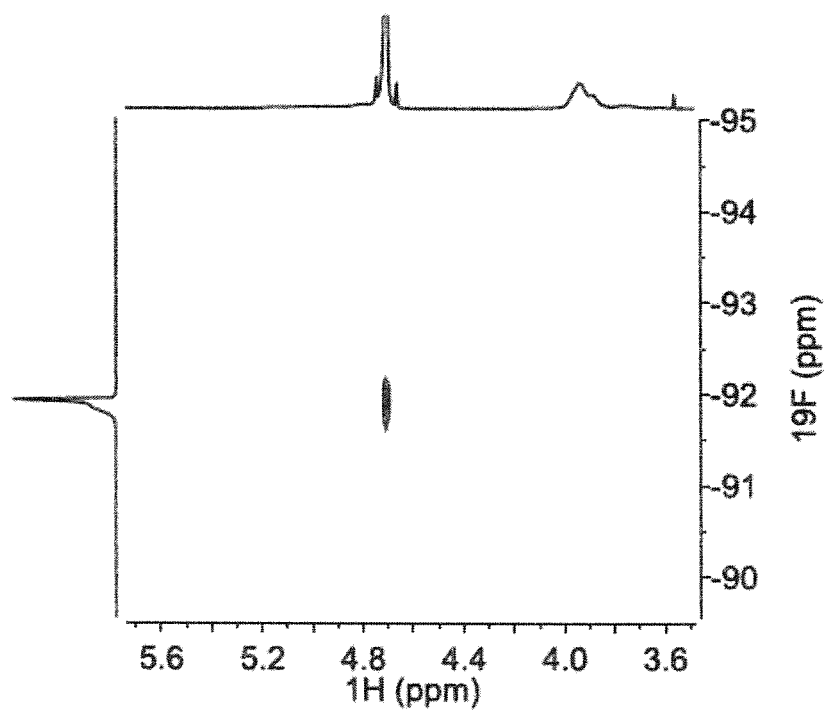
FIG. 3 shows Hetero-nuclear Overhauser Enhancement Spectroscopy (HOESY) NMR measured on beads comprising PLGA and PFCE without gadoteridol according to the invention. HOESY between water-protons and fluorine can be detected. This indicates a homogeneous structure with small sized perfluorocarbon domains distributed in the polymeric matrix. Nanoparticles in $D_2O$, 500 MHz ($^1H$), 471 MHz ($^{19}F$).
Figure 4:
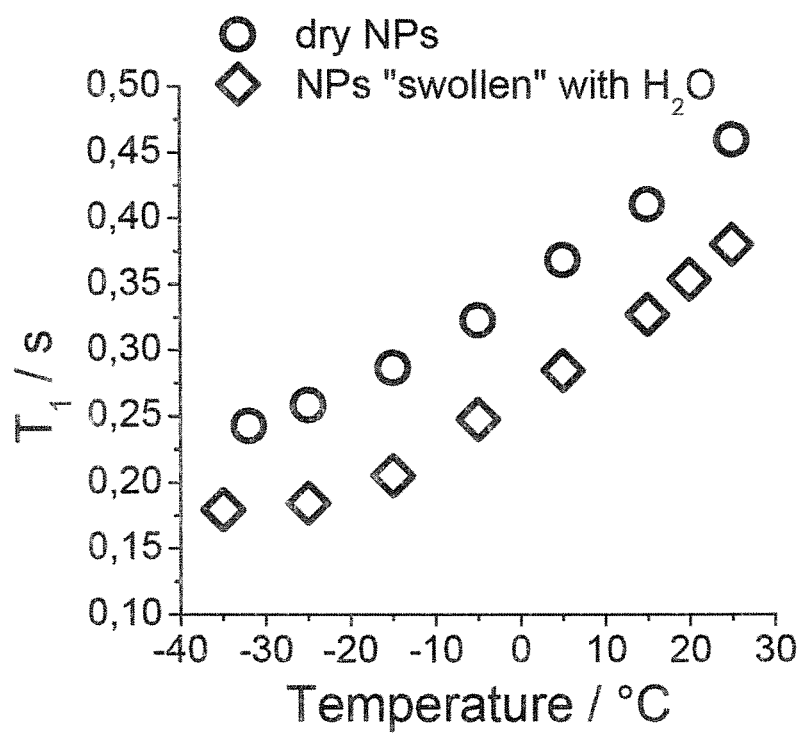
FIG. 4 shows solid state NMR measured on beads comprising PLGA, PFCE and gadoteridol according to the invention, which are in a dry state and a water-swollen state.
Figure 5:
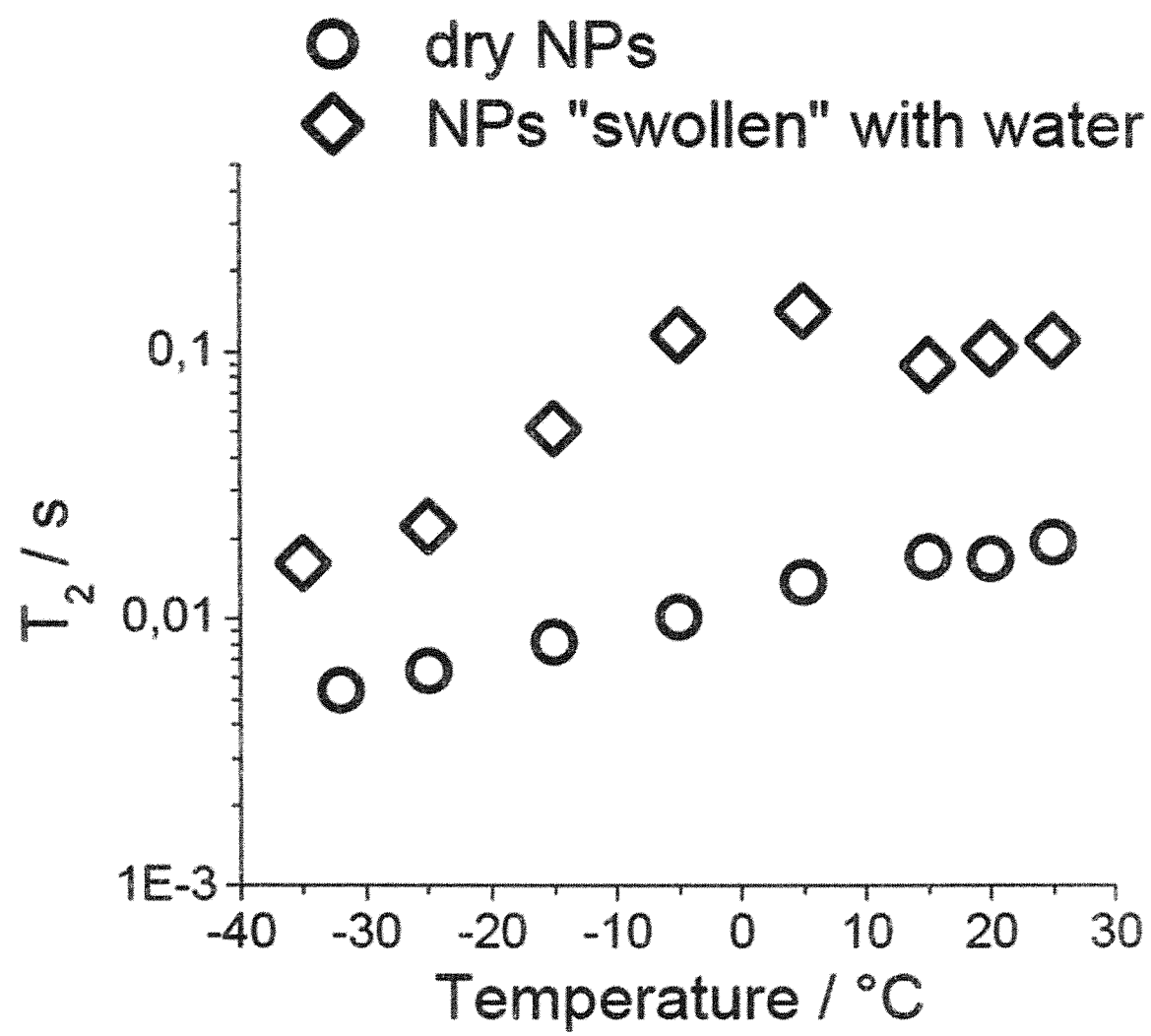
FIG. 5 shows solid state NMR measured on beads comprising PLGA, PFCE and gadoteridol according to the invention, which are in a dry state and a water-swollen state.
Figure 6:
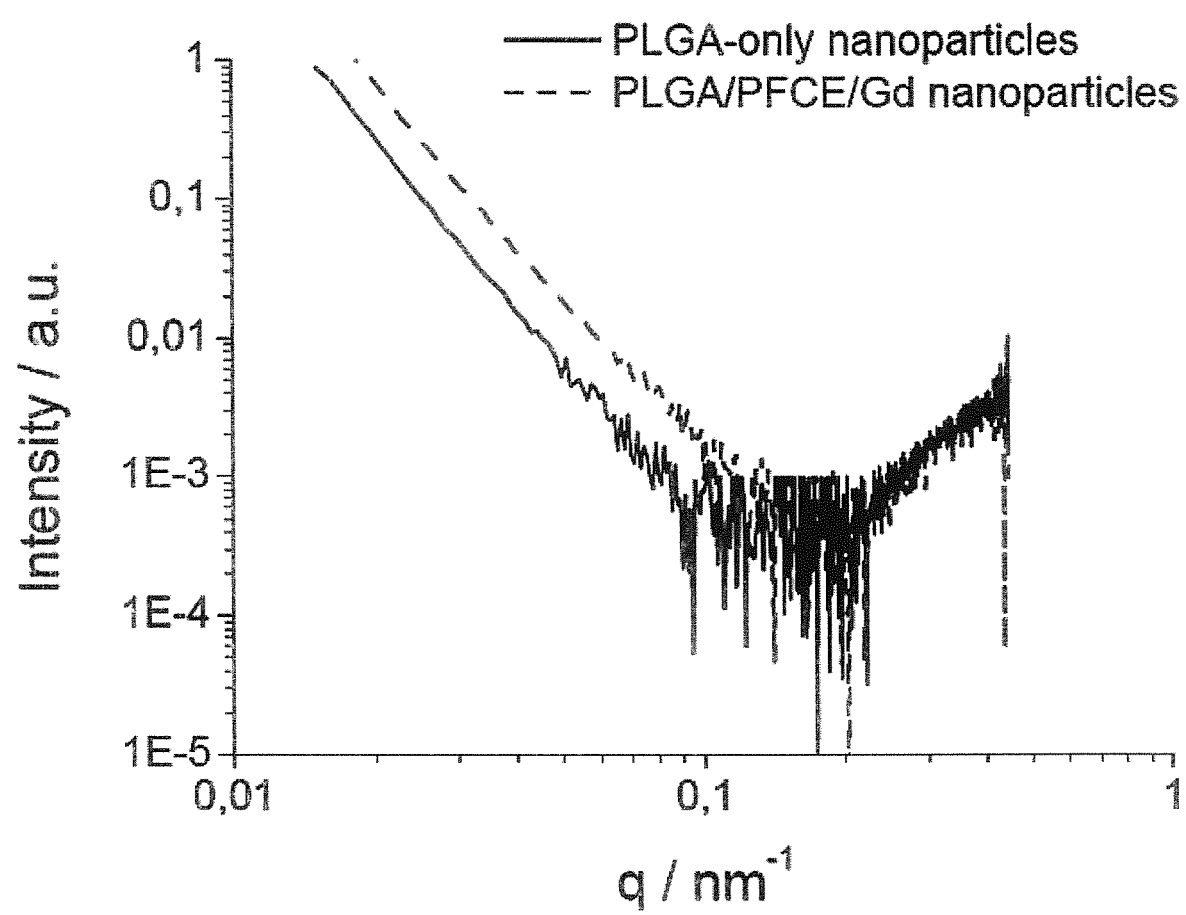
FIG. 6 shows small angle X-ray scattering results of the beads comprising PLGA, PFCE and gadoteridol (line with higher intensity) and the beads comprising PLGA without PFCE and gadoteridol (line with lower intensity). The results are similar, which may suggest that the particles are homogeneous full sphere or particle with polydisperse PFCE-filled pores.
Figure 7:
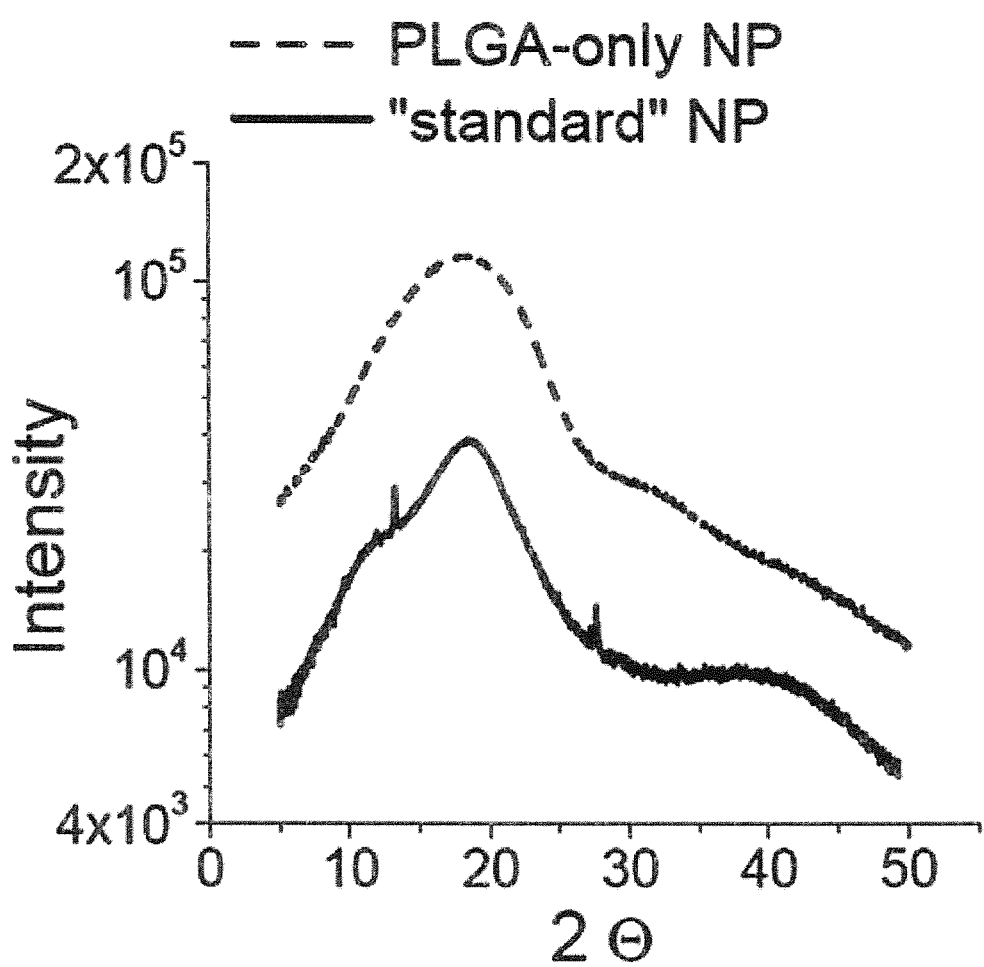
Figure 8:
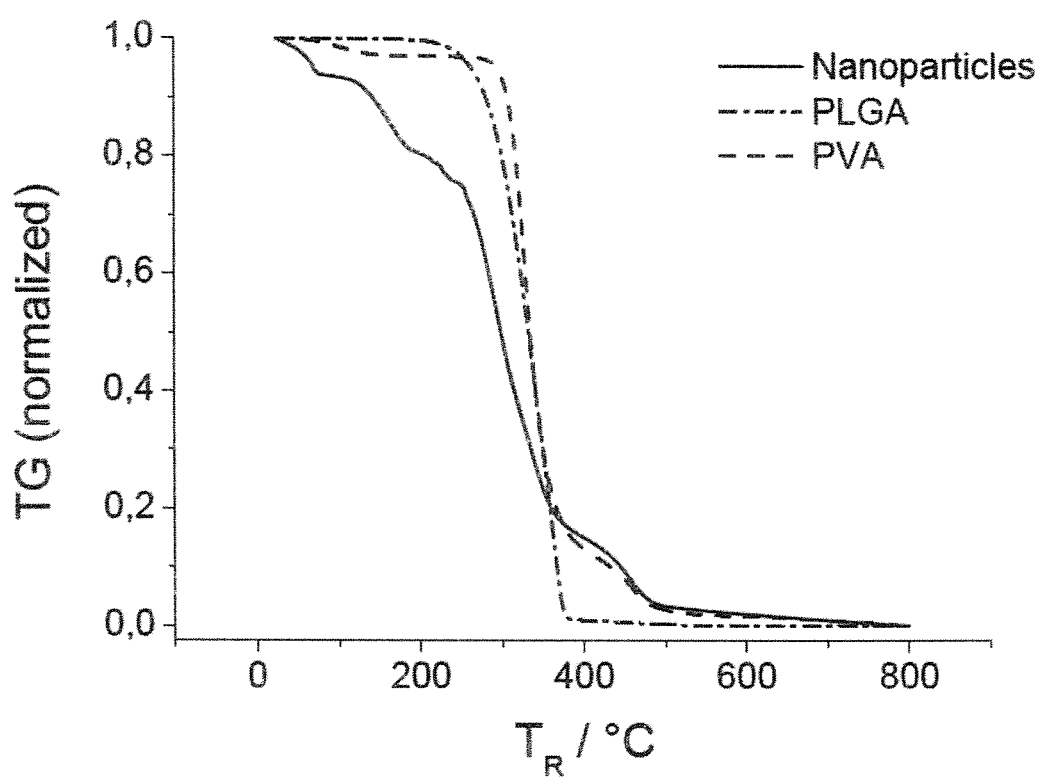
FIG. 8 shows results of thermogravimetric (TGA) analysis of the beads comprising PLGA, PFCE and gadoteridol according to the invention, PLGA and PGA. The shoulder at 400° C. in the result of the beads according to the invention indicates the presence of PVA in the beads.
Figure 9:
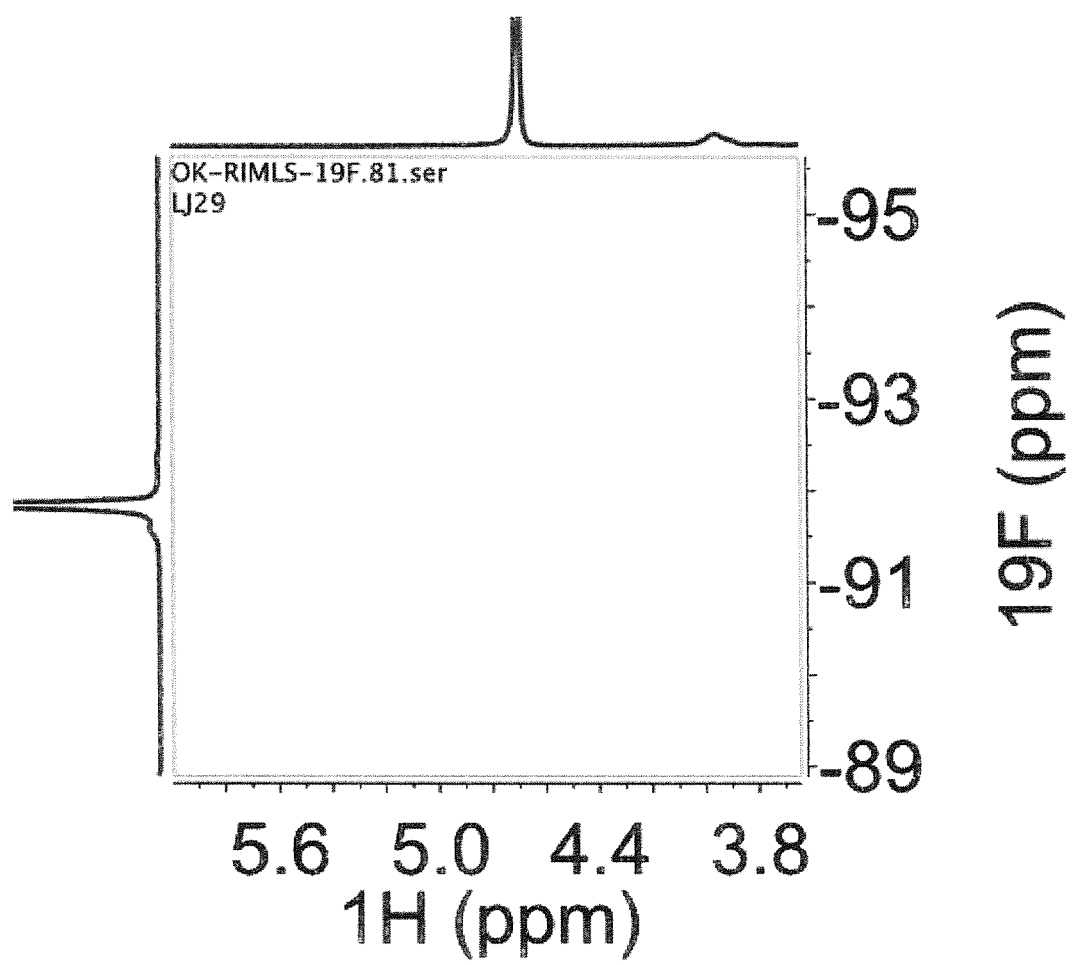
FIG. 9 shows HOESY measurement of experiment 15 (comparative). HOESY NMR of PFCE-loaded core-shell capsules in D2O. The cross-peak between water and PFCE (approx. −92 ppm y-axis 4.8 ppm x-axis) is almost not present, showing that fluorine does not interact with water. The residual signal is coming from the region where the PFCE core is in contact with the shell. 400 MHz ($^1$H), 377 MHz ($^{19}$F).
Figure 10:
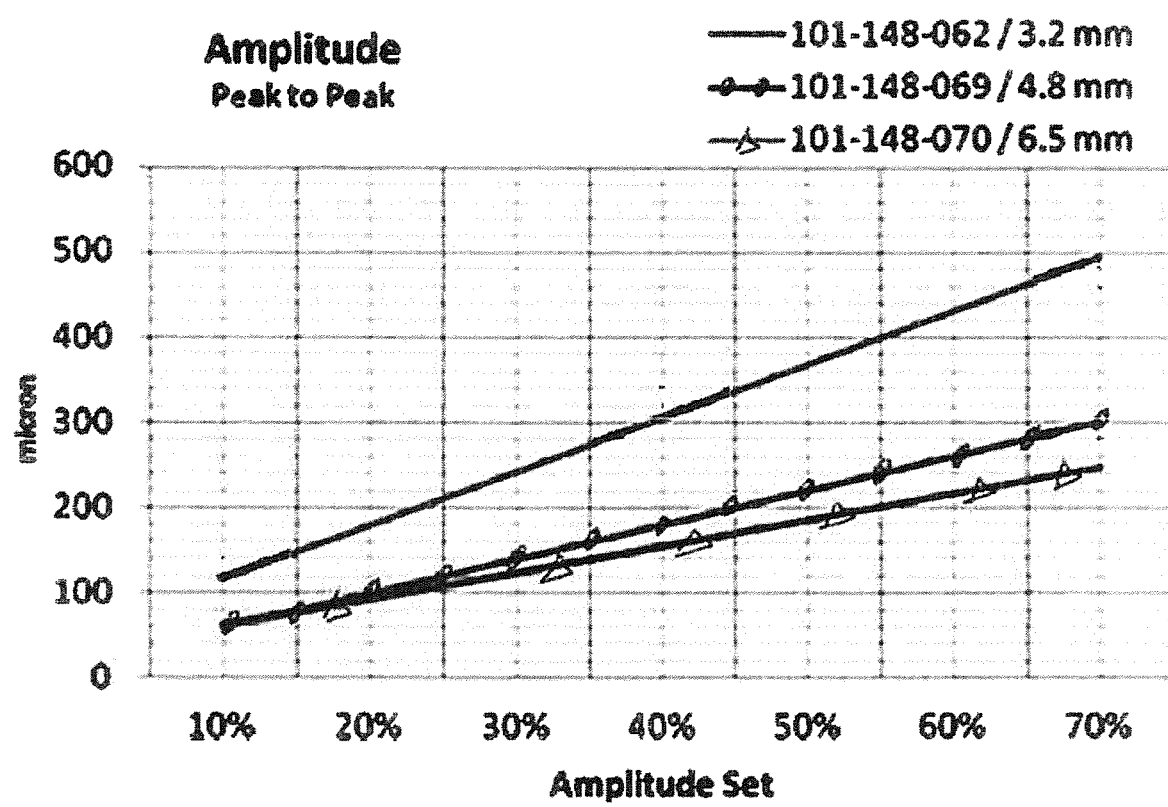
FIG. 10 shows the relation between amplitude and power on sonicators having different microtips. A microtip of 3.2 mm gives the highest amplitude at a certain amplitude setting, followed by a microtip of 4.8 and 6.5 mm respectively.

In contrast to our particles this nano-capsules show almost no HOESY between F-atoms in PFCE and water (FIG. 9) in NMR. Due to core-shell structure of these capsules, water cannot penetrate inside the superhydrophobic PFCE core. Therefore, almost no interaction between water and PFCE is present. The slight residual HOESY signal could result from the contact area of the core with the shell i.e. the interface of the PFCE filling with the PLGA shell. In contrast our particles show extensive HOESY between water protons and fluorine atoms in PFCE (FIG. 3). Due to the homogenous multi-domain structure of our particles that is stabilized by hydrophilic PVA, the contact area between water and PFCE is much higher resulting in stronger HOESY.

Remarks

HOESY cannot be measured with Gd-containing particles, as Gd is paramagnetic. The prior art (Pisani) missed essential details on how to perform the experiments. The inventors used their sonicator for making these capsules, so they could not use the exact sonication settings from literature. They do not believe that this is important for obtaining capsules.

The method the inventors used was based on several papers from that group in combination of with one of their PhD thesis. The problem was that they often published non-completed methods (e.g. skipped volume of surfactant).

ssNMR of swollen capsules could not be measured, as they are not that stable in concentrated aqueous solution and ssNMR takes several hours.

What is claimed is:

1. A process for the preparation of beads having a multi-domain structure comprising a biocompatible hydrophobic polymer, a perfluorocarbon, polyvinylalcohol (PVA) and optionally a metal compound, comprising the steps of:
   a) adding the perfluorocarbon and optionally the metal compound to a solution of the biocompatible hydrophobic polymer in a polar solvent to provide a first liquid mixture;
   b) adding the first liquid mixture to an aqueous solution including the PVA as a first biocompatible surfactant and optionally a second biocompatible surfactant under sonication to obtain a second liquid mixture;
   c) maintaining the sonication of the second liquid mixture while cooling;
   d) evaporating the polar solvent from the second liquid mixture to obtain a suspension of beads comprising the biocompatible hydrophobic polymer, the perfluorocarbon and optionally the metal compound;
   e) separating the beads from the suspension and preparing a water suspension of the beads; and
   f) freeze-drying the water suspension to obtain the beads, wherein the beads have multiple perfluorocarbon domains distributed in a matrix comprising the biocompatible hydrophobic polymer and the PVA;
   wherein the addition of the first liquid mixture to the aqueous solution in step b) is performed within a period of at most 10 seconds,
   wherein the sonication in step b) and the sonication in step c) are performed directly to the liquid mixtures at an amplitude of at least 120 μm for 0.01-10 minutes and
   wherein the weight ratio of the PVA and optionally the second biocompatible surfactant to the biocompatible hydrophobic polymer is at least 3:1.

2. The process according to claim 1, wherein step a) involves adding the perfluorocarbon and the metal compound to the solution of the biocompatible hydrophobic polymer, wherein the metal compound is added without prior dilution or as a solution comprising at least 100 mg of the metal compound per mL of the solution and wherein the first liquid mixture obtained is an emulsion.

3. The process according to claim 1, wherein step a) is performed under direct sonication.

4. The process according to claim 1, wherein the biocompatible hydrophobic polymer comprises a polymer selected from the group consisting of poly(lactic-co-glycolic) acid, polylactic acid), poly(caprolactone), polydimethylsiloxane and combinations thereof.

5. The process according to claim 1, wherein the polar solvent is selected from the group consisting of dichloromethane, chloroform, ethyl acetate and combinations thereof.

6. The process according to claim 1, wherein the perfluorocarbon is selected from the group consisting of perfluoro crown ether, perfluoro octyl bromide, perfluorooctane, perfluoro poly ethers and combinations and modifications thereof.

7. The process according to claim 1, wherein the metal compound comprises gadolinium.

8. The process according to claim 1, wherein the second biocompatible surfactant is present and is selected from the group consisting of a polysorbate and polyvinylpyrrolidone.

9. The process according to claim 1, wherein the weight ratio of the perfluorocarbon in the first liquid mixture with respect to the biocompatible hydrophobic polymer in the first liquid mixture is between 10:1 to 25:1, or between 12:1 to 20:1, or between 14:1 to 18:1.

10. The process according to claim 1, wherein the weight ratio of the metal compound in the first liquid mixture with respect to the biocompatible hydrophobic polymer in the first liquid mixture is between 1:1000 to 1:100, or between 1:500 to 1:150, or between 1:300 to 1:180.

11. The process according to claim 1, wherein the weight ratio of the biocompatible surfactant with respect to the biocompatible hydrophobic polymer is between 4:1 to 10:1, or between 4.5:1 to 8:1 or between 4.8:1 to 6:1.

12. The process according to claim 1, wherein step a) is performed under direct sonication, using a probe.

13. The process according to claim 1, wherein step a) is performed under direct sonication, using a flow sonicator.

* * * * *